(12) United States Patent
Perry et al.

(10) Patent No.: US 9,351,980 B2
(45) Date of Patent: May 31, 2016

(54) DI-ASPIRIN DERIVATIVES

(75) Inventors: Christopher John Perry, West Midlands (GB); Iain Douglas Nicholl, West Midlands (GB)

(73) Assignee: The University of Wolverhampton, West Midlands (GB)

( * ) Notice: Subject to any disclaimer, the term of this patent is extended or adjusted under 35 U.S.C. 154(b) by 0 days.

(21) Appl. No.: 13/578,934

(22) PCT Filed: Feb. 15, 2011

(86) PCT No.: PCT/GB2011/050284
§ 371 (c)(1),
(2), (4) Date: Oct. 26, 2012

(87) PCT Pub. No.: WO2011/098839
PCT Pub. Date: Aug. 18, 2011

(65) Prior Publication Data
US 2013/0035317 A1 Feb. 7, 2013

(30) Foreign Application Priority Data
Feb. 15, 2010 (GB) .................................. 10025302

(51) Int. Cl.
| | |
|---|---|
| *A61K 31/60* | (2006.01) |
| *A61K 31/609* | (2006.01) |
| *A61K 31/616* | (2006.01) |
| *A61K 31/621* | (2006.01) |
| *C07C 69/24* | (2006.01) |
| *C07C 69/40* | (2006.01) |
| *C07C 69/44* | (2006.01) |
| *C07C 69/60* | (2006.01) |
| *C07C 69/63* | (2006.01) |
| *C07C 69/76* | (2006.01) |
| *C07C 69/78* | (2006.01) |
| *C07C 69/82* | (2006.01) |
| *C07C 69/96* | (2006.01) |
| *C07C 205/43* | (2006.01) |
| *C07C 235/60* | (2006.01) |
| *C07C 235/88* | (2006.01) |

(52) U.S. Cl.
CPC ............... *A61K 31/60* (2013.01); *A61K 31/609* (2013.01); *A61K 31/616* (2013.01); *A61K 31/621* (2013.01); *C07C 69/24* (2013.01); *C07C 69/40* (2013.01); *C07C 69/44* (2013.01); *C07C 69/60* (2013.01); *C07C 69/63* (2013.01); *C07C 69/76* (2013.01); *C07C 69/78* (2013.01); *C07C 69/82* (2013.01); *C07C 69/96* (2013.01); *C07C 205/43* (2013.01); *C07C 235/60* (2013.01); *C07C 235/88* (2013.01)

(58) Field of Classification Search
USPC .................. 514/165, 166, 159, 160
See application file for complete search history.

(56) References Cited

U.S. PATENT DOCUMENTS

| | | | |
|---|---|---|---|
| 4,474,750 | A | 10/1984 | Gaffar et al. |
| 4,529,719 | A | 7/1985 | Tye |
| 5,041,615 | A | 8/1991 | Hai et al. |
| 5,599,959 | A | 2/1997 | Hosmane et al. |
| 6,037,338 | A * | 3/2000 | Guttag ........................... 514/165 |
| 2004/0033997 | A1 | 2/2004 | Baron |
| 2005/0282734 | A1 | 12/2005 | Kadima et al. |
| 2009/0197854 | A1 | 8/2009 | Karlin |

FOREIGN PATENT DOCUMENTS

| | | |
|---|---|---|
| WO | WO 03/046034 | 6/2003 |
| WO | WO 2005/039545 | 5/2005 |
| WO | WO 2005/076987 | 8/2005 |

OTHER PUBLICATIONS

Erdmann, L., et al. Biomaterials. vol. 21 pp. 1941-1946. Published 2000.*
Bak, A.W., et al., Life Sciences vol. 62, pp. PL367-PL373. Published 1998.*
Zaugg, R.H., et al. The Journal of Biological Chemistry vol. 255, pp. 2816-2821. Published 1980.*
Moriarty, L. et al (J. Med. Chem., vol. 51, pp. 7991-7999, published 2008).*
Prabhudesai and coworkers (Journal of Surgical Oncology vol. 96 pp. 77-88 published 2007).*
Barnes et al (British Journal of Cancer vol. 77, pp. 573-580 published 1998).*
Moriarty et al (J. Med. Chem. vol. 51, pp. 7991-7999 published 2008).*
Pereira et al (Carcinogenesis vol. 15, pp. 1049-1054 published 1994).*
Chan, R. et al., Annals of Oncology vol. 15 pp. 996-999 (2004).*
Barnes and Lee, "Chemoprevention of spontaneous intestinal adenomas in the adenomatous polyposis coli *min* mouse model with aspirin," Gastroenterology. 114:873-877 (1998).
Baron et al., "A randomized trial of aspirin to prevent colorectal adenomas," The New England Journal of Medicine. 348(10): 891-899 (2003).
Carmichael et al., "Evaluation of a tetrazolium-based semiautomated colorimetric assay: assessment of chemosensitivity testing," Cancer Research. 47: 936-942 (1987).
Chan et al., "Aspirin use and survival after diagnosis of colorectal cancer," JAMA 302(6):649-659 (2009).
Cheng et al., "Microarry analysis of vanillin-regulated gene expression profile," Pharmacological Research. 56:474-482 (2007).
Cheng and Desreumaux, "5-aminosalicylic acid is an attractive candidate agent for chemoprevention of colon cancer in patients with inflammatory bowel disease," World J Gastroenterol. 11(3):309-314 (2005).

(Continued)

Primary Examiner — Paul Zarek
Assistant Examiner — George W Kosturko
(74) Attorney, Agent, or Firm — Greenberg Traurig, LLP; Fang Xie

(57) ABSTRACT

The invention relates to the use of di-aspirin (bis(2-carboxyphenyl)succinate) and its derivatives in the treatment of colon and colorectal cancer. It also relates to novel derivatives of di-aspirin and to a method of synthesis of the di-aspirin and its derivatives.

2 Claims, 7 Drawing Sheets

(56) References Cited

OTHER PUBLICATIONS

Dihlmann et al., "The nonsteroidal anti-inflammatory drugs aspirin and indomethacin attenuate β-catenin/TCT-4 signaling," Oncogene. 20:645-653 (2001).
Din et al., "Evidence for colorectal cancer cell specificity of aspirin effects on NFkB signaling and apoptosis," British Journal of Cancer. 91: 381-388 (2004).
Ferrández et al., "COX-2 and colorectal cancer," Current Pharmaceutical Design. 9:2229-2251 (2003).
Gasche et al., "Mesalazine improves replication fidelity in cultured colorectal cells," Cancer Res. 65(10): 3993-3997 (2005).
Giovannucci, E., "The prevention of colorectal cancer by aspirin use," Biomed & Pharmacother. 53: 303-308 (1999).
Goel, et al., A novel mechanism for aspirin-mediated growth inhibition of human colon cancer cells, Clinical Cancer Research. 9:383-390 (2003).
Gordon, A.J., "Acetylsalicylamide O- to N- Migration," Tetrahedron. 23:867-870 (1967).
Hsu and Li, "Aspirin potently inhibits oxidative DNA strand breaks: implications for cancer chemoprevention," Biochemical and Biophysical Research Communications. 293: 705-709 (2002).
Hussey et al., "Novel anti-tumour activity of 2, 3, 5-trimethyl-6-(3-pyridylmethyl)-1,4-benzoquinone (CV-6504) against established murine adenocarcinomas (MAC), " British Journal of Cancer 73:1187-1192 (1996).
Imperiale, "Aspirin and the prevention of colorectal cancer," The New England Journal of Medicine. 348(10): 879-880 (2003).
Kahns and Bundgaard, "N-Acyl derivatives as prodrug forms for amides: Chemical stability and enzymatic hydrolysis of various N-acyl and N-alkoxycarbonyl amide derivatives," International Journal of Pharmaceuticals. 71:31-43 (1991).
Kim et al., "Inhibition of cell proliferation and invasion in a human colon cancer cell line by 5-aminosalicylic acid," Digestive and Liver Disease. 41:328-337 (2009).
Kim et al., "Pretreatment of acetylsalicylic acid promotes tumor necrosis factor-related apoptosis-inducing ligand-induced apoptosis by down-regulating BCL-2 Gene Expression," Journal of Biological Chemistry. 280(49): 41047-41056 (2005).
King et al., "Antimutagenicity of cinnamaldehyde and vanillin in human cells: Global gene expression and possible role of DNA damage and repair," Mutation Research 616: 60-69 (2007).
Kopp and Ghosh., "Inhibition of NF-kB by sodium salicylate and aspirin," Science. 265: 956-959 (1994).
Krishnan et al., "Aspirin and other prostaglandin inhibitors for the prevention of colon cancer," Infusion Chemotherapy-Irradiation Interactions. Chapter 38. 405-422 (1998).
Lai et al., Mechanisms underlying aspirin-mediated growth inhibition and apoptosis induction of cyclooxygenase-2 negative colon cancer cell line SW480, World J. Gastroenterol. 14(26): 4227-4233 (2008).
McIlhatton et al., "Nitric oxide-donating aspirin derivatives suppress microsatellite instability in mismatch repair-deficient and hereditary nonpolyposis colorectal cancer cells," Cancer Res. 67(22): 10966-10975 (2007).
Mosmann, Tim. "Rapid colorimetric assay for cellular growth and survival: application to proliferation and cytotoxicity assays," Journal of Immunological Methods. 65: 55-63 (1983).
Narayan and Roy. "Role of APC and DNA mismatch repair genes in the development of colorectal cancers," Molecular Cancer. 2(41): 1-15 (2003).
Paterson et al., "The identification of salicylates as normal constituents of serum: a link between diet and health?" J. Clin. Pathol. 51: 502-505 (1998).

Paterson and Lawrence. "Salicylic acid: a link between aspirin, diet and the prevention of colorectal cancer," Q. J. Med. 94: 445-448 (2001).
Patrignani, Paola, "Nonsteroidal anti-inflammatory drugs, COX-2 and colorectal cancer," Toxicology Letters. 112-113:493-498 (2000).
Richter et al., "Growth inhibition and induction of apoptosis in colorectal tumour cells by cyclooxygenase inhibitors," Carcinogenesis. 22(1):17-25 (2001).
Rigas, B., "Novel agents for cancer prevention based on nitric oxide," Biochemical Society Transactions. 35(5): 1364-1368 (2007).
Ruschoff et al., "Aspirin suppresses the mutator phenotype associated with hereditary nonpolyposis colorectal cancer by genetic selection," Proc. Natl. Acad. Sci. 95: 11301-11306 (1998).
Sansom et al., "Suppression of intestinal and mammary neoplasia by lifetime administration of aspirin in $Apc^{Min/+}$ and $Apc^{Min/+}$, $Msh2^{-/-}$ Mice[1]," Cancer Research. 61: 7060-7064 (2001).
Smith et al., "The effect of non-steroidal anti-inflammatory drugs on human colorectal cancer cells: evidence of different mechanisms of action," European Journal of Cancer. 36: 664-674 (2000).
Stark et al., "Aspirin activates the NF-kB signaling pathway and induces apoptosis in intestinal neoplasia in two in vivo models of human colorectal cancer," Carcinogenesis. 28(5): 968-976 (2007).
Stark et al., "Aspirin-induced activation of the NF-kB signaling pathway: a novel mechanism for aspirin-mediated apoptosis in colon cancer cells," The FASEB Journal. 15: 1273-1275 (2001).
Strul and Arber, "Non-steroidal anti-inflammatory drugs and selective apoptotic anti-neoplastic drugs in the prevention of colorectal cancer: The role of super aspirins," IMAJ. 2: 695-702 (2000).
Tesei et al., "NCX 4040, and NO-donating acetylsalicylic acid derivative: Efficacy and mechanisms of action in cancer cells," Nitric Oxide. 19: 225-236 (2008).
Thun et al., "Nonsteroidal anti-inflammatory drugs as anticancer agents: mechanistic, pharmacologic, and clinical issues," Journal of National Cancer Institute. 94(4): 252-266 (2002).
Watson, Alastair., "An overview of apoptosis and the prevention of colorectal cancer," Critical Reviews in Oncology/Hematology. 57:107-121 (2006).
West et al., "Colorectal cancer screening in Europe: differences in approach; similar barriers to overcome," Int. J. Colorectal Dis. 1-10 (2009).
Williams et al., "Aspirin Use and Potential Mechanisms for colorectal Cancer Prevention," The Journal of Clinical Investigations. 100(6):1325-1329 (1997).
Williams et al., "Growth inhibition of human colon cancer cells by nitric oxide (NO)-donating aspirin is associated with cycloozygenase-2 induction and β-catenin/T-cell factor signaling, nuclear factor-kB, and NO Synthase 2 Inhibition: Implications for Chemoprevention," Cancer Research. 63:7613-7618 (2003).
Yin et al., "The anti-inflammatory agents aspirin and salicylate inhibit the activity of IkB kinase-β," Nature. 396: 77-80 (1998).
Yu et al., "Inhibition of cytosolic phospholipase A2 mRNA expression: a novel mechanism for acetylsalicylic acid-mediated growth inhibition and apoptosis in colon cancer cells," Regulatory Peptides. 114:101-107 (2003).
Zerbini et al., "A novel pathway involving melanoma differentiation associate gene-7/interleukin-24 mediates nonsteroidal anti-inflammatory drug-induced apoptosis and growth arrest of cancer cells," Cancer Res. 66(24): 11922-11931 (2006).
Zerbini et al., "NF-kB-mediated repression of growth arrest- and DNA-damage-inducible proteins 45α and $^γ$ is essential for cancer cell survival," PNAS 101(37): 13615-13623 (2004).
Sandler, R.S., et al, "A randomised trial of aspirin to prevent a colorectal adenomas in patients with previous colorectal cancer." The New England Journal of Medicine 2003, 348(10): 883-890.
"The Merck Index," Thirteenth Ed., 2001, Merck & Co., Inc., p. 1494.

* cited by examiner

DI-ASPIRIN DERIVATIVES

RELATED APPLICATIONS

This application is a National Phase application of International Application No. PCT/GB2011/050284 filed Feb. 15, 2011, which claims priority to and the benefit of GB 1002530.2 filed Feb. 15, 2010, and the contents of both applications are incorporated by reference herein in their entirety.

FIELD OF THE INVENTION

The invention relates to the use of di-aspirin (bis(2-carboxyphenyl)succinate) and its derivatives in the treatment of colon and colorectal cancer. It also relates to novel derivatives of di-aspirin and to a method of synthesis of the di-aspirin and its derivatives.

BACKGROUND OF THE INVENTION

Cancers of the bowel, most commonly known as colorectal cancer or colon cancer, are among the most frequent malignancies in economically developed countries (Giovannucci, E.; 1999) and are the third most common cancer in Western countries (Narayan & Roy, 2003). Globally, colorectal cancers cause significant morbidity and mortality, with one million new cases per year, and make up 9% of all cancers diagnosed.

Screening by faecal occult blood tests and flexible sigmoidoscopy is theoretically the most effective means of prevention, however these method are not straightforward for high-risk populations and are not cost-effective.

Although several therapeutic agents approved for the treatment of colorectal cancer are available, they all share the disadvantages of either low response rates and/or unfavourable side-effect profile. Platinum analogues such as carboplatin and oxaliplatin cause problematic side-effects of myelo-suppression and peripheral neurotoxicity and also suffer from low response rates. The new drug cetuximab and other monoclonal antibody-based therapies seem to be dependent on the patient's genotype, with large sections of the population having mutations leading to poor response.

There is abundant epidemiological and experimental evidence that regular ingestion of non-steroidal anti-inflammatory drugs (NSAIDs) including acetylsalicylic acid (aspirin) promotes colorectal tumour regression and reduces the relative risk of developing colorectal cancer. There is also substantive evidence that aspirin is specifically cytotoxic against colorectal cancer cells cultured in vitro. However, gastrointestinal toxicity, heartburn and vomiting, renal disturbances and neurological related side-effects preclude the universality of aspirin both as a chemopreventitive agent and as a therapeutic agent.

SUMMARY OF THE INVENTION

According to a first aspect of the invention, there is provided the use of a compound of Formula (I) in the treatment of colorectal cancer;

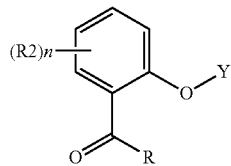
(I)

wherein Y represents H or —C(=O)—X
wherein X represents:
(i)(a) $C_{1-12}$alkyl optionally substituted by one or more of $C_{1-12}$alkyl, halogen or —O—$NO_2$,
(b) $C_{5-12}$aryl optionally substituted by one or more of halogen, —$CO_2H$, —CN, —OH, —$NH_2$, —$CONH_2$, $C_{1-6}$alkyl, $C_{1-6}$alkenyl, —$NO_2$, —$SO_3H$, or —$SO_3Na$,
(c) $C_{2-12}$alkenyl optionally substituted by one or more of halogen, —$CO_2H$, —CN, —OH, —$NH_2$, —$CONH_2$, $C_{1-6}$alkyl, $C_{1-6}$alkenyl, —$NO_2$, —$SO_3H$, or —$SO_3Na$,
each of (a)-(c) being substituted with the following structure by attachment through the carbon of the —C(O)O group of the structure

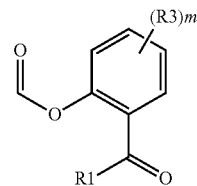

(ii) $C_{2-6}$alkyl substituted with one or more carboxyl group;
(iii) $C_{1-12}$alkyl optionally substituted by one or more of halogen, —$CO_2H$, —CN, —OH, —$NH_2$, —$CONH_2$, $C_{1-6}$alkyl, $C_{1-6}$alkenyl, —$NO_2$, —$SO_3H$, or —$SO_3Na$;
(iv) $C_{5-10}$aryl optionally substituted by one or more of halogen, —$CO_2H$, —CN, —OH, —$NH_2$, —$CONH_2$, $C_{1-6}$alkyl, $C_{1-6}$alkenyl, —$NO_2$, —$SO_3H$, or —$SO_3Na$
wherein when Y represents —C(=O)—X, R and R1 are independently selected from —OH and —$NH_2$
wherein when Y represents H, R represents —NHC(=O)—$C_{1-6}$alkyl
R2 and R3 are independently selected from halogen, $C_{1-12}$alkyl, hydroxyl, carboxyl, $C_{1-12}$alkoxy, —$NH_2$, —NH($C_{1-6}$alkyl), —N($C_{1-6}$alkyl)($C_{1-6}$alkyl), $C_{1-12}$alkyl-$NH_2$, $C_{1-12}$alkyl-NH($C_{1-6}$alkyl), $C_{1-12}$alkyl-N($C_{1-6}$alkyl)($C_{1-6}$alkyl), $C_{1-12}$alkyl-C(=O)—$NH_2$, $C_{1-12}$alkyl-C(=O)—NH($C_{1-6}$alkyl), $C_{1-12}$alkyl-C(=O)—N($C_{1-6}$alkyl)($C_{1-6}$alkyl), —$NO_2$, —$SO_3H$ and —$SO_3Na$
and n and m are independently selected from 0, 1, 2, 3 or 4, with the proviso that where X is $CH_3$, then R is —$NH_2$.

According to a first aspect of the invention, there is provided a compound of Formula (I) for use in the treatment of colorectal cancer;

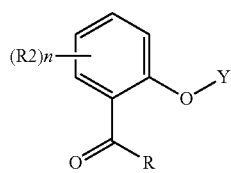
(I)

wherein Y represents H or —C(=O)—X
wherein X represents:
(i)(a) $C_{1-12}$alkyl optionally substituted by one or more of $C_{1-12}$alkyl, halogen or —O—NO$_2$,
(b) $C_{5-12}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na,
(c) $C_{2-12}$alkenyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na,
each of (a)-(c) being substituted with the following structure by attachment through the carbon of the —C(O)O group of the structure

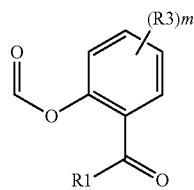

(ii) $C_{2-6}$alkyl substituted with one or more carboxyl group;
(iii) $C_{1-12}$alkyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na;
(iv) $C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na;
v) $C_{1-6}$alkoxy optionally substituted by one or more halogen, —OH, OC$_{1-6}$alkyl, primary, secondary or tertiary amino where the N-substituents are $C_{1-6}$alkyl;
vi) —O—$C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na
wherein when Y represents —C(=O)—X, R and R1 are independently selected from —OH, —NH$_2$ and $C_{1-8}$alkoxy
wherein when Y represents H, R represents —NHC(=O)—$C_{1-6}$alkyl
R2 and R3 are independently selected from halogen, $C_{1-12}$alkyl, hydroxyl, carboxyl, $C_{1-12}$alkoxy, —NH$_2$, —NH($C_{1-6}$alkyl), —N($C_{1-6}$alkyl)($C_{1-6}$alkyl), $C_{1-12}$alkyl-NH$_2$, $C_{1-12}$alkyl-NH($C_{1-6}$alkyl), $C_{1-12}$alkyl-N($C_{1-6}$alkyl)($C_{1-6}$alkyl), $C_{1-12}$alkyl-C(=O)—NH$_2$, $C_{1-12}$alkyl-C(=O)—NH($C_{1-6}$alkyl), $C_{1-12}$alkyl-C(=O)—N($C_{1-6}$alkyl)($C_{1-6}$alkyl), —NO$_2$, —SO$_3$H and —SO$_3$Na
and n and m are independently selected from 0, 1, 2, 3 or 4, with the proviso that where X is CH$_3$, then R is —NH$_2$.

In one embodiment where Y represents —C(=O)—X, X represents $C_{1-12}$alkyl optionally substituted by one or more of $C_{1-12}$alkyl, halogen or —O—NO$_2$ and substituted with the following structure by attachment through the carbon of the —C(O)O group of the structure

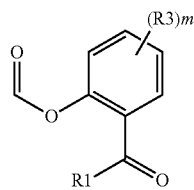

The $C_{1-12}$alkyl may be —CH$_2$CH$_2$—, —CH$_2$(CH$_2$)$_2$CH$_2$— or —CH$_2$(CH$_2$)$_6$CH$_2$—.

In one embodiment the $C_{1-12}$alkyl may be substituted by one or more of halogen or —O—NO$_2$. The substituted $C_{1-12}$alkyl may be —CHBrCHBr— or —CH(—O—NO$_2$)CH(O—NO$_2$)—.

In one embodiment where Y represents —C(=O)—X, X represents $C_{5-12}$aryl substituted with the following structure by attachment through the carbon of the —C(O)O group of the structure

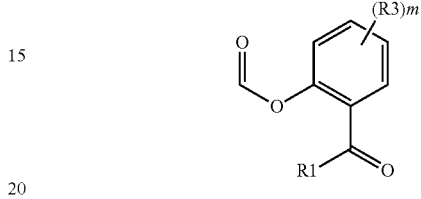

$C_{5-12}$aryl may be phenyl.

In one embodiment where Y represents —C(=O)—X, X represents $C_{2-12}$alkenyl substituted with the following structure by attachment through the carbon of the —C(O)O group of the structure

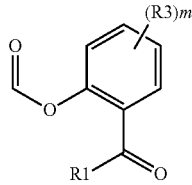

$C_{2-12}$alkenyl may be —CH=CH—, in particular —CH=CH— (trans).

In one embodiment where Y represents —C(=O)—X, X represents —CH$_2$CH$_2$C(O)OH.

In one embodiment where Y represents —C(=O)—X, X represents $C_{1-5}$alkyl or $C_{1-6}$alkyl. X may represent —CH$_3$. X may represent —CH$_2$CH$_3$, —CH$_2$CH$_2$CH$_3$, —CH$_2$(CH$_2$)$_2$CH$_3$, —CH$_2$(CH$_2$)$_3$CH$_3$, —CH$_2$(CH$_2$)$_4$CH$_3$.

In one embodiment where Y represents —C(=O)—X, X represents phenyl, or phenyl substituted with a bromo or methyl group, for example m-bromophenyl or p-methylphenyl. In one embodiment when X represents phenyl R represents —OCH$_3$. In one embodiment when X represents m-bromophenyl R represents —OCH(CH$_3$)$_2$.

In one embodiment where Y represents —C(=O)—X, X represents $C_{1-6}$alkoxy optionally substituted by one or more halogen. X may represent —OCH$_3$, —OCH$_2$CH$_3$, —OCH$_2$(CH$_2$)$_2$CH$_3$ or —OCH$_2$(CH$_2$)$_2$CH$_2$Cl.

In one embodiment where Y represents —C(=O)—X, X represents —O—$C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na. X may represent —O—C$_6$H$_5$ or —O—C$_6$H$_5$ substituted in the para position with —NO$_2$.

In one embodiment when Y represents H, R represents —NHC(=O)—CH$_3$.

In one embodiment, there is provided a compound of Formula (I) for use in the treatment of colorectal cancer, wherein Y represents —C(=O)—X and X represents —CH$_2$CH$_2$—C(=O)—O—C$_6$H$_4$—C(=O)R1. In this embodiment R and R1 may each represent —OH. Alternatively R and R1 may each represent —NH$_2$. In this embodiment n and m may be 0.

In one embodiment, there is provided a compound of Formula (I) for use in the treatment of colorectal cancer, wherein Y represents —C(=O)—X and X represents —CHBrCHBr—C(=O)—O—C$_6$H$_4$—C(=O)R1. In this embodiment R and R1 may each represent —OH. In this embodiment n and m may be 0.

In one embodiment, there is provided a compound of Formula (I) for use in the treatment of colorectal cancer, wherein Y represents —C(=O)—X and X represents —CH(—O—NO$_2$)CH(O—NO$_2$)—C(=O)—O—C$_6$H$_4$—C(=O)R1. In this embodiment R and R1 may each represent —OH. In this embodiment n and m may be 0.

In one embodiment, there is provided a compound of Formula (I) for use in the treatment of colorectal cancer, wherein Y represents —C(=O)—X and X represents —CH$_2$(CH$_2$)$_2$CH$_2$—C(=O)—O—C$_6$H$_4$—C(=O)R1. In this embodiment R and R$^1$ may each represent —OH. Alternatively R and R$^1$ may each represent —NH$_2$. In this embodiment n and m may be 0.

In one embodiment, there is provided a compound of Formula (I) for use in the treatment of colorectal cancer, wherein Y represents —C(=O)—X and X represents —CH$_2$(CH$_2$)$_6$CH$_2$—C(=O)—O—C$_6$H$_4$—C(=O)R1. In this embodiment R and R1 may each represent —OH. Alternatively R and R1 may each represent —NH$_2$. In this embodiment n and m may be 0.

In one embodiment, there is provided a compound of Formula (I) for use in the treatment of colorectal cancer, wherein Y represents —C(=O)—X and X represents —CH=CH—C(=O)—O—C$_6$H$_4$—C(=O)R1. In this embodiment R and R$^1$ may each represent —OH. Alternatively R and R1 may each represent —NH$_2$. In this embodiment n and m may be 0. In this embodiment the —CH=CH— may be trans —CH=CH—.

In one embodiment, there is provided a compound of Formula (I) for use in the treatment of colorectal cancer, wherein Y represents —C(=O)—X and X represents —C$_6$H$_4$—C(=O)—O—C$_6$H$_4$—C(=O)R1. In this embodiment R and R1 may each represent —OH. Alternatively R and R1 may each represent —NH$_2$. In this embodiment n and m may be 0. In this embodiment the —C$_6$H$_4$— of X may have the attached groups para or ortho to each other.

In one embodiment, there is provided a compound of Formula (I) for use in the treatment of colorectal cancer, wherein Y represents —C(=O)—X and X represents —CH$_2$CH$_2$C(=O)OH. In this embodiment R may represent —OH. In this embodiment n may be 0.

In one embodiment, there is provided a compound of Formula (I) for use in the treatment of colorectal cancer, wherein Y represents —C(=O)—X and X represents —C$_6$H$_5$. In this embodiment R may represent —OH. In this embodiment n may be 0.

In one embodiment, there is provided a compound of Formula (I) for use in the treatment of colorectal cancer, wherein Y represents —C(=O)—X and X represents —C$_6$H$_4$Br. In this embodiment R may represent —OH. In this embodiment n may be 0. In this embodiment the Br may be positioned in the meta position.

In one embodiment, there is provided a compound of Formula (I) for use in the treatment of colorectal cancer, wherein Y represents —C(=O)—X and X represents —C$_6$H$_4$CH$_3$. In this embodiment R may represent —OH. In this embodiment n may be 0. In this embodiment the —CH$_3$ may be positioned in the para position.

In one embodiment, there is provided a compound of Formula (I) for use in the treatment of colorectal cancer, wherein Y represents —C(=O)—X and X represents —CH$_3$. In this embodiment R represents —NH$_2$. In this embodiment n may be 0.

In one embodiment, there is provided a compound of Formula (I) for use in the treatment of colorectal cancer, wherein Y represents —C(=O)—X and X represents —CH$_2$CH$_3$, —CH$_2$CH$_2$CH$_3$, —CH$_2$(CH$_2$)$_2$CH$_3$, —CH$_2$(CH$_2$)$_3$CH$_3$ or —CH$_2$(CH$_2$)$_4$CH$_3$. In this embodiment R represents —OH. In this embodiment n may be 0.

In one embodiment, there is provided a compound of Formula (I) for use in the treatment of colorectal cancer, wherein Y represents —C(=O)—X, X represents C$_{1-6}$alkoxy optionally substituted by one or more halogen. X may represent —OCH$_3$, —OCH$_2$CH$_3$, —OCH$_2$(CH$_2$)$_2$CH$_3$ or —OCH$_2$(CH$_2$)$_2$CH$_2$Cl. In this embodiment R represents —OH. In this embodiment n may be 0.

In one embodiment, there is provided a compound of Formula (I) for use in the treatment of colorectal cancer, wherein Y represents —C(=O)—X, X represents —OC$_6$H$_5$ or —OC$_6$H$_5$ substituted in the para position by —NO$_2$. In this embodiment R represents —OH. In this embodiment n may be 0.

In one embodiment, there is provided a compound of Formula (I) for use in the treatment of colorectal cancer, wherein Y represents —C(=O)—X, X represents -phenyl and R represents —OCH$_3$. In this embodiment n may be 0.

In one embodiment, there is provided a compound of Formula (I) for use in the treatment of colorectal cancer, wherein Y represents —C(=O)—X, X represents -m-bromophenyl and R represents —OCH(CH$_3$)$_2$. In this embodiment n may be 0.

In one embodiment, there is provided a compound of Formula (I) for use in the treatment of colorectal cancer, wherein Y represents H and R represents —NHC(=O)—CH$_3$ In one embodiment, there is provided a compound of Formula (I) for use in the treatment of colorectal cancer;

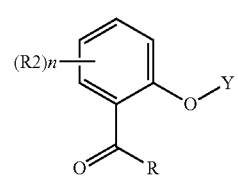

wherein Y represents H or —C(=O)—X
wherein X represents:
(i)(a) C$_{1-12}$alkyl, for example C$_{2-8}$alkyl,
(b) C$_{5-12}$aryl, for example C$_6$aryl,
(c) C$_{2-12}$alkenyl, for example C$_2$alkenyl,
each of (a)-(c) being substituted with the following structure by attachment through the carbon of the —C(O)O group of the structure

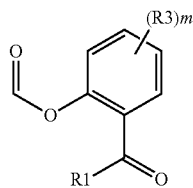

(ii) $C_{5-10}$aryl, for example $C_6$aryl, optionally substituted by one or more of halogen or $C_{1-6}$alkyl;
wherein when Y represents —C(=O)—X, R and R1 are independently selected from —OH, —NH$_2$ and $C_{1-8}$alkoxy, for example $C_{1-3}$alkoxy
wherein when Y represents H, R represents —NHC(=O)—$C_{1-6}$alkyl, for example —NHC(=O)—CH$_3$;
and n and m are 0.

According to a second aspect of the invention there is provided a compound of Formula (I) wherein Y represents H or —C(=O)—X and X represents:
(i)(a) $C_{1-12}$alkyl optionally substituted by one or more of $C_{1-12}$alkyl, halogen or —O—NO$_2$,
(b) $C_{5-12}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na, or
(c) $C_{2-6}$alkenyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na,
each of (a)-(c) being substituted with the following structure by attachment through the carbon of the —C(O)O group of the structure

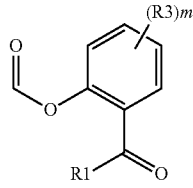

(ii) $C_{2-6}$alkyl substituted with one or more carboxyl groups,
(iii) $C_{1-12}$alkyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na, or
(iv) $C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na
wherein when Y represents —C(=O)—X, R and R1 are independently selected from —OH and —NH$_2$
wherein when Y represents H, R represents —NHC(=O)—$C_{1-6}$alkyl
R2 and R3 are independently selected from halogen, $C_{1-12}$alkyl, hydroxyl, carboxyl, $C_{1-12}$alkoxy, —NH$_2$, —NH($C_{1-6}$alkyl), —N($C_{1-6}$alkyl)($C_{1-6}$alkyl), $C_{1-12}$alkyl-NH$_2$, $C_{1-12}$alkyl-NH($C_{1-6}$alkyl), $C_{1-12}$alkyl-N($C_{1-6}$alkyl)($C_{1-6}$alkyl), $C_{1-12}$alkyl-C(=O)—NH$_2$, $C_{1-12}$alkyl-C(=O)—NH($C_{1-6}$alkyl), $C_{1-12}$alkyl-C(=O)—N($C_{1-6}$alkyl)($C_{1-6}$alkyl), —NO$_2$, —SO$_3$H and —SO$_3$Na
and n and m are independently selected from 0, 1, 2, 3 or 4
with the proviso that one or both of R and R1 are —NH$_2$ when X represents:
$C_{1-12}$alkyl or $C_{2-6}$alkenyl, each substituted with the following structure by attachment through the carbon of the —C(O)O group of the structure

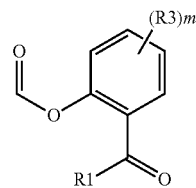

and with the further proviso that when X is —CH$_3$, R is —NH$_2$.

According to a second aspect of the invention there is provided a compound of Formula (I) wherein Y represents H or —C(=O)—X and X represents:
(i)(a) $C_{1-12}$alkyl optionally substituted by one or more of $C_{1-12}$alkyl, halogen or —O—NO$_2$,
(b) $C_{5-12}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na, or
(c) $C_{2-6}$alkenyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na,
each of (a)-(c) being substituted with the following structure by attachment through the carbon of the —C(O)O group of the structure

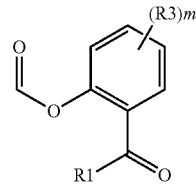

(ii) $C_{2-6}$alkyl substituted with one or more carboxyl groups,
(iii) $C_{1-12}$alkyl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na, or
(iv) $C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na;
v) $C_{1-6}$alkoxy optionally substituted by one or more halogen, —OH, O$C_{1-6}$alkyl, primary, secondary or tertiary amino where the N-substituents are $C_{1-6}$alkyl;
vi) —O—$C_{5-10}$aryl optionally substituted by one or more of halogen, —CO$_2$H, —CN, —OH, —NH$_2$, —CONH$_2$, $C_{1-6}$alkyl, $C_{1-6}$alkenyl, —NO$_2$, —SO$_3$H, or —SO$_3$Na
wherein when Y represents —C(=O)—X, R and R1 are independently selected from —OH, —NH$_2$ and $C_{1-8}$alkoxy
wherein when Y represents H, R represents —NHC(=O)—$C_{1-6}$alkyl
R2 and R3 are independently selected from halogen, $C_{1-12}$alkyl, hydroxyl, carboxyl, $C_{1-12}$alkoxy, —NH$_2$, —NH($C_{1-6}$alkyl), —N($C_{1-6}$alkyl)($C_{1-6}$alkyl), $C_{1-12}$alkyl-NH$_2$, $C_{1-12}$alkyl-NH($C_{1-6}$alkyl), $C_{1-12}$alkyl-N($C_{1-6}$alkyl)($C_{1-6}$alkyl), $C_{1-12}$alkyl-C(=O)—NH$_2$, $C_{1-12}$alkyl-C(=O)—NH($C_{1-6}$alkyl), $C_{1-12}$alkyl-C(=O)—N($C_{1-6}$alkyl)($C_{1-6}$alkyl), —NO$_2$, —SO$_3$H and —SO$_3$Na
and n and m are independently selected from 0, 1, 2, 3 or 4
with the proviso that one or both of R and R1 are —NH$_2$ when X represents:
$C_{1-12}$alkyl or $C_{2-6}$alkenyl, each substituted with the following structure by attachment through the carbon of the —C(O)O group of the structure

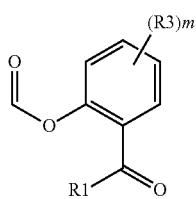

and with the further proviso that when X is —CH$_3$, R is —NH$_2$.

In one embodiment where Y represents —C(=O)—X, X represents C$_{1-12}$alkyl substituted with the following structure by attachment through the carbon of the —C(O)O group of the structure

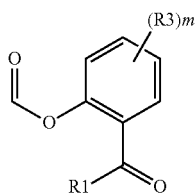

The C$_{1-12}$alkyl may be —CH$_2$CH$_2$—, —CH$_2$(CH$_2$)$_2$CH$_2$— or —CH$_2$(CH$_2$)$_6$ or —CH$_2$(CH$_2$)$_6$CH$_2$—. In one embodiment the C$_{1-12}$alkyl may be substituted by one or more of halogen or —O—NO$_2$. The substituted C$_{1-12}$alkyl may be —CHBrCHBr— or —CH(—O—NO$_2$)CH(O—NO$_2$)—.

In one embodiment where Y represents —C(=O)—X, X represents C$_{5-12}$aryl substituted with the following structure by attachment through the carbon of the —C(O)O group of the structure

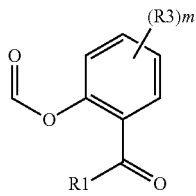

C$_{5-12}$aryl may be phenyl.

In one embodiment where Y represents —C(=O)—X, X represents C$_{2-12}$alkenyl substituted with the following structure by attachment through the carbon of the —C(O)O group of the structure

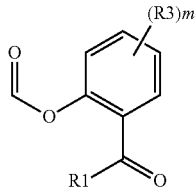

C$_{2-12}$alkenyl may be —CH=CH—, in particular —CH=CH— (trans).

In one embodiment where Y represents —C(=O)—X, X represents —CH$_2$CH$_2$C(O)OH.

In one embodiment where Y represents —C(=O)—X, X represents C$_{1-5}$alkyl or C$_{1-6}$alkyl. X may represent —CH$_3$. X may represent —CH$_2$CH$_3$, —CH$_2$CH$_2$CH$_3$, —CH$_2$(CH$_2$)$_2$CH$_3$, —CH$_2$(CH$_2$)$_3$CH$_3$, —CH$_2$(CH$_2$)$_4$CH$_3$ In one embodiment where Y represents —C(=O)—X, X represents phenyl, or phenyl substituted with a bromo or methyl group, for example m-bromophenyl or p-methylphenyl. In one embodiment when X represents phenyl R represents —OCH$_3$. In one embodiment when X represents m-bromophenyl R represents —OCH(CH$_3$)$_2$.

In one embodiment where Y represents —C(=O)—X, X represents C$_{1-6}$alkoxy optionally substituted by one or more halogen. X may represent —OCH$_3$, —OCH$_2$CH$_3$, —OCH$_2$(CH$_2$)$_2$CH$_3$ or —OCH$_2$(CH$_2$)$_2$CH$_2$Cl.

In one embodiment where Y represents —C(=O)—X, X represents —O—C$_{5-10}$aryl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na (to cover 530 and 531, is this list of possible substituent too broad?). X may represent —O—C$_6$H$_5$ or —O—C$_6$H$_5$ substituted in the para position with —NO$_2$.

In one embodiment when Y represents H, R represents —NHC(=O)—CH$_3$.

In one embodiment, there is provided a compound of Formula (I), wherein Y represents —C(=O)—X and X represents —CH$_2$CH$_2$—C(=O)—O—C$_6$H$_4$—C(=O)R1. In this embodiment R and R1 each represent —NH$_2$. In this embodiment n and m may be 0.

In one embodiment, there is provided a compound of Formula (I), wherein Y represents —C(=O)—X and X represents —CHBrCHBr—C(=O)—O—C$_6$H$_4$—C(=O)R1. In this embodiment R and R1 may each represent —OH. In this embodiment n and m may be 0.

In one embodiment, there is provided a compound of Formula (I), wherein Y represents —C(=O)—X and X represents —CH(—O—NO$_2$)CH$_2$(O—NO$_2$)—C(=O)—O—C$_6$H$_4$—C(=O)R1. In this embodiment R and R1 may each represent —OH. In this embodiment n and m may be 0.

In one embodiment, there is provided a compound of Formula (I), wherein Y represents —C(=O)—X and X represents —CH$_2$(CH$_2$)$_6$CH$_2$—C(=O)—O—C$_6$H$_4$—C(=O)R1. In this embodiment R and R1 each represent —NH$_2$. In this embodiment n and m may be 0.

In one embodiment, there is provided a compound of Formula (I), wherein Y represents —C(=O)—X and X represents —CH=CH—C(=O)—O—C$_6$H$_4$—C(=O)R1. In this embodiment R and R1 each represent —NH$_2$. In this embodiment n and m may be 0. In this embodiment the —CH=CH— may be trans —CH=CH—.

In one embodiment, there is provided a compound of Formula (I), wherein Y represents —C(=O)—X and X represents —C$_6$H$_4$—C(=O)—O—C$_6$H$_4$—C(=O)R1. In this embodiment R and R1 may each represent —OH. Alternatively R and R1 may each represent —NH$_2$. In this embodiment n and m may be 0. In this embodiment the —C$_6$H$_4$— of X may have the attached groups para or ortho to each other.

In one embodiment, there is provided a compound of Formula (I), wherein Y represents —C(=O)—X and X represents —CH$_2$CH$_2$C(=O)OH. In this embodiment R may represent —OH. In this embodiment n may be 0.

In one embodiment, there is provided a compound of Formula (I), wherein Y represents —C(=O)—X and X represents —C$_6$H$_5$. In this embodiment R may represent —OH. In this embodiment n may be 0.

In one embodiment, there is provided a compound of Formula (I), wherein Y represents —C(=O)—X and X represents —C$_6$H$_4$Br. In this embodiment R may represent —OH.

In this embodiment n may be 0. In this embodiment the Br may be positioned in the meta position.

In one embodiment, there is provided a compound of Formula (I), wherein Y represents —C(=O)—X and X represents —C$_6$H$_4$CH$_3$. In this embodiment R may represent —OH. In this embodiment n may be 0. In this embodiment the —CH$_3$ may be positioned in the para position.

In one embodiment, there is provided a compound of Formula (I), wherein Y represents —C(=O)—X and X represents —CH$_3$. In this embodiment R may represent —NH$_2$. In this embodiment n may be 0.

In one embodiment, there is provided a compound of Formula (I), wherein Y represents —C(=O)—X and X represents —CH$_2$CH$_3$, —CH$_2$CH$_2$CH$_3$, —CH$_2$ (CH$_2$)$_2$CH$_3$, —CH$_2$ (CH$_2$)$_3$CH$_3$ or —CH$_2$ (CH$_2$)$_4$CH$_3$. In this embodiment R represents —OH. In this embodiment n may be 0.

In one embodiment, there is provided a compound of Formula (I), wherein Y represents —C(=O)—X, X represents C$_{1-6}$alkoxy optionally substituted by one or more halogen. X may represent —OCH$_3$, —OCH$_2$CH$_3$, —OCH$_2$(CH$_2$)$_2$CH$_3$ or —OCH$_2$(CH$_2$)$_2$CH$_2$Cl. In this embodiment R represents —OH. In this embodiment n may be 0.

In one embodiment, there is provided a compound of Formula (I), wherein Y represents —C(=O)—X, X represents —OC$_6$H$_5$ or —OC$_6$H$_5$ substituted in the para position by —NO$_2$. In this embodiment R represents —OH. In this embodiment n may be 0.

In one embodiment, there is provided a compound of Formula (I), wherein Y represents —C(=O)—X, X represents -phenyl and R represents —OCH$_3$. In this embodiment n may be 0.

In one embodiment, there is provided a compound of Formula (I), wherein Y represents —C(=O)—X, X represents -m-bromophenyl and R represents —OCH(CH$_3$)$_2$. In this embodiment n may be 0.

In one embodiment, there is provided a compound of Formula (I), wherein Y represents H and R represents —NHC(=O)—CH$_3$ According to a further aspect of the invention there is provided a compound of Formula (I) wherein Y represents H or —C(=O)—X and X represents:
(i)(a) C$_{1-12}$alkyl optionally substituted by one or more of C$_{1-12}$alkyl, halogen or —O—NO$_2$,
(b) C$_{5-12}$aryl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na,
(c) C$_{2-12}$alkenyl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na,
each of (a)-(c) being substituted with the following structure by attachment through the carbon of the —C(O)O group of the structure

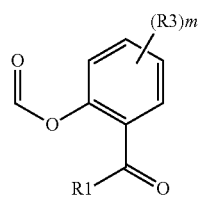

(ii) C$_{2-6}$alkyl substituted with one or more carboxyl group;
(iii) C$_{1-12}$alkyl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na;

(iv) C$_{5-10}$aryl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na;
v) C$_{1-6}$alkoxy optionally substituted by one or more halogen, —OH, OC$_{1-6}$alkyl, primary, secondary or tertiary amino where the N-substituents are C$_{1-6}$alkyl;
vi) —O—C$_{5-10}$aryl optionally substituted by one or more of halogen, —CO$_2$H, —CN, —OH, —NH$_2$, —CONH$_2$, C$_{1-6}$alkyl, C$_{1-6}$alkenyl, —NO$_2$, —SO$_3$H, or —SO$_3$Na;
wherein when Y represents —C(=O)—X, R and R1 are independently selected from —OH, —NH$_2$ and C$_{1-8}$alkoxy
wherein when Y represents H, R represents —NHC(=O)—C$_{1-6}$alkyl
R2 and R3 are independently selected from halogen, C$_{1-12}$alkyl, hydroxyl, carboxyl, C$_{1-12}$alkoxy, —NH$_2$, —NH(C$_{1-6}$alkyl), —N(C$_{1-6}$alkyl)(C$_{1-6}$alkyl), C$_{1-12}$alkyl-NH$_2$, C$_{1-12}$alkyl-NH(C$_{1-6}$alkyl), C$_{1-12}$alkyl-N(C$_{1-6}$alkyl)(C$_{1-6}$alkyl), C$_{1-12}$alkyl-C(=O)—NH$_2$, C$_{1-12}$alkyl-C(=O)—NH(C$_{1-6}$alkyl), C$_{1-12}$alkyl-C(=O)—N(C$_{1-6}$alkyl)(C$_{1-6}$alkyl), —NO$_2$, —SO$_3$H and —SO$_3$Na
and n and m are independently selected from 0, 1, 2, 3 or 4, with the proviso that where X is CH$_3$, then R is —NH$_2$.

The term C$_{1-12}$alkyl is used to refer to a linear or branched saturated hydrocarbon group having from 1 to 12 carbon atoms. The number of carbon atoms can be varied by varying the numerical range indicated in the term and therefore for example C$_{4-6}$alkyl has 4 to 6 carbon atoms in the group.

The term C$_{1-12}$alkoxy is used to refer to an —O—C$_{1-12}$alkyl group wherein C$_{1-12}$alkyl is as defined above.

The term C$_{5-12}$ aryl is used to refer to a functional group or substituent derived from an aromatic ring having from 5 to 12 carbon atoms. The number of carbon atoms can be varied by varying the numerical range indicated in the term.

The term C$_{2-6}$alkenyl is used to refer to a linear or branched unsaturated, hydrocarbon group having from 2 to 6 carbon atoms and having with one or more carbon-carbon double bonds. The number of carbon atoms in the group can be varied by varying the numerical range indicated in this term and therefore for example C$_{4-6}$alkenyl has 4 to 6 carbon atoms in the group.

The term halogen or halo is used to refer to fluorine, chlorine, bromine or iodine.

Compounds of Formula (I) have advantageously been shown to be toxic to the SW480 cell line, a cell recognised to be derived from a colorectal carcinoma. The compounds have further been shown to be significantly more effective than monomeric aspirin in cell death assays. In one embodiment, certain compounds of Formula (I) reduced the survival rate of SW480 cells to roughly 60% of the survival rate in the presence of an equal concentration of monomeric aspirin. In another embodiment, certain compounds of Formula (I) reduced the survival rate of SW480 cells to roughly 40% of the survival rate in the presence of an equal concentration of monomeric aspirin. In a further embodiment, certain compounds of Formula (I) reduced the survival rate of SW480 cells to roughly 20% of the survival rate in the presence of an equal concentration of monomeric aspirin.

The compounds of Formula (I) have further shown some selectivity for the colon carcinoma derived cell line SW480 as compared to cell lines derived from other cancers, for example MDA-231-MB cells which are a breast cancer-derived cell line. In one embodiment, the di-aspirin in the cell viability assay was significantly more toxic to SW480 colorectal cancer cells than to MDA-231-MB cells.

It is thought by the inventors that the compounds of interest in this invention act in inhibiting DNA methyltransferase (DNA MTase) and/or Histone deacetylases (HDAC).

Any one of the compounds of Formula (I) could be used as an intermediate in the manufacture of another compound within Formula (I). According to a further aspect there is provided an intermediate of Formula (I).

In one embodiment, there is provided an intermediate of Formula (I), wherein X represents —CHBrCHBr—C(=O)—O—$C_6H_4$—C(=O)R1. In this embodiment R and R1 may each represent —OH. In this embodiment n and m may be 0.

DETAILED DESCRIPTION OF THE INVENTION

Uses of the Compounds

Figure 1:
FIG. 1 shows an in vitro toxicity assay of a compound of Formula (I)

The invention provides a method for treating or preventing these diseases, the method comprising administering to a patient in need thereof a therapeutically effective amount of the compound of Formula (I). By analogy, it is also within the scope of the invention to use the compounds of Formula (I) in the manufacture of a medicament for said disease.

It will be appreciated that the term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs.

Combination Therapies

Many diseases are treated using more than one medicament in the treatment, either concomitantly administered or sequentially administered. It is therefore within the scope of the invention to use the compounds of Formula (I) in therapeutic methods for the treatment of colorectal cancer in combination with one another, or as an adjunct to, or in conjunction with other established therapies normally used in the treatment of said disease. By analogy, it is also within the scope of the invention to use the compounds of Formula (I) in combination with other therapeutically active compounds normally used in the treatment of colorectal cancer in the manufacture of a medicament for said disease.

Examples of such combination therapies may include administration of a compound according to the present invention in combination with a medicament useful for treating colorectal cancer such as oxaliplatin, carboplatin or monoclonal antibody therapies.

The combination treatment may be carried out in any way as deemed necessary or convenient by the person skilled in the art and for the purpose of this specification, no limitations with regard to the order, amount, repetition or relative amount of the compounds to be used in combination is contemplated.

Pharmaceutical Compositions

According to another aspect of the invention, there is provided a pharmaceutical composition comprising a compound as defined in the second aspect of the invention, or a pharmaceutically acceptable salt, solvate or hydrate thereof.

In one embodiment, there is provided a pharmaceutical composition comprising a compound of Formula (I), or a pharmaceutically acceptable salt, solvate or hydrate thereof for use in the treatment of colorectal cancer.

In another embodiment there is provided the use of a compound of Formula (I) in the manufacture of a medicament for the treatment of colorectal cancer.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, volume 66, issue 2. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. In addition, the compounds of the invention may form solvates with water or common organic solvents. Such solvates are also encompassed within the scope of the present invention.

The composition may further comprise a buffer system, preservative(s), tonicity agent(s), chelating agent(s), stabilizers and surfactants, which is well known to the skilled person. For convenience reference is made to Remington: The Science and Practice of Pharmacy, 20th edition, 2000. The composition may also further comprise one or more therapeutic agents active against the same disease state.

Methods to produce controlled release systems useful for compositions of the current invention include, but are not limited to, crystallization, condensation, co-crystallization, precipitation, co-precipitation, emulsification, dispersion, high pressure homogenisation, en-capsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Administration of pharmaceutical compositions according to the invention may be through several routes of administration, for example, oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

For topical use, sprays, creams, ointments, jellies, gels, inhalants, dermal patches, implants, solutions of suspensions, etc., containing the compounds of the present invention are contemplated. For the purpose of this application, topical applications shall include mouth washes and gargles.

Pharmaceutical compositions for oral administration include solid dosage forms such as hard or soft capsules, tablets, troches, dragees, pills, lozenges, powders and granules and liquid dosage forms for oral administration include solutions, emulsions, aqueous or oily suspensions, syrups and elixirs, each containing a predetermined amount of the active ingredient, and which may include a suitable excipient.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations.

Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874 to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as a solvent or suspending medium. For this purpose, any bland fixed oil may be employed using synthetic mono- or diglycerides. In addition, fatty acids such as oleic acid find use in the preparation of injectables.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the prolactin receptor antagonist in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use.

The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Depot injectable formulations are also contemplated as being within the scope of the present invention.

When the use of the invention is combined with a second therapeutic agent active against the same disease state, they may conveniently be administered alone or in combination, in either single or multiple doses, sequentially or simultaneously, by the same route of administration, or by a different route.

According to another aspect of the invention there is provided a method for treating or preventing colorectal cancer, the method comprising administering to a patient in need thereof a therapeutically effective amount of a compound or composition as hereinbefore defined.

Effective Dosages

The use of the compounds of Formula (I), or compositions thereof, will generally be in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the systems associated with the underlying disorder. Therapeutic benefit also includes halting or slowing the progression of the disease, regardless of whether improvement is realised.

The exact dosage will depend upon the frequency and mode of administration, the sex, age, weight and general condition of the subject treated, the nature and severity of the condition treated and any concomitant diseases to be treated and other factors evident to those skilled in the art. Determination of the effective dosage is well within the capabilities of those skilled in the art.

When a compound of the invention or a pharmaceutically acceptable salt, solvate or pro-drug thereof is used in combination with a second therapeutic agent active against the same disease state the dose of each compound may differ from that when the compound is used alone. Appropriate doses will be readily appreciated by those skilled in the art.

Methods of Synthesis

It will be appreciated that the compounds of Formula (I) may be synthesised via a variety of different routes using commercially available starting materials and/or starting materials prepared by conventional methods.

According to a further aspect of the invention, there is provided a process for preparing a compound of Formula (I), comprising the steps of:

dissolving salicylic acid, or an ester derivative thereof, in THF and pyridine, adding a suitable acid chloride in cases where Y is —CO—X with X=(ii)-(iv), or a di-acid chloride in cases where Y is —CO—X with X=(i)(a)-(i)(c), removing the pyridine hydrochloride by quenching with water, and efficient stirring and recovering the precipitate.

According to a further aspect of the invention, there is provided a process for preparing a compound of Formula (I), comprising the steps of:

dissolving salicylic acid, or an ester derivative thereof, in pyridine, adding a suitable acid chloride in cases where Y is —CO—X with X=(ii)-(iv), or a di-acid chloride in cases where Y is —CO—X with X=(i)(a)-(i)(c), removing the pyridine hydrochloride by quenching with water, and efficient stirring and recovering the precipitate. The aforementioned method is of use in particular where R represents $C_{1-8}$alkoxy.

In one embodiment, the solution of salicylic acid in pyridine is stirred until the salicylic acid is dissolved before the acid chloride added. The addition of the acid chloride may be slowly under vigorous stirring. The stirring may be continued for at least 1 hour, for example 1 to 18 hours. The mixture may then be poured into cold water and stirred, for example for up to 1 hour. The crystalline precipitate formed may be recovered by filtering.

In one embodiment the reaction mixture is subject to stirring, preferably mechanical stirring, throughout the entire reaction time.

In one embodiment, salicylic acid and pyridine are present in the solution at a final concentration of between 0.5M and 5M, acid chloride is present in the solution at a final concentration of between 0.2M and 2.5 M prior to precipitation.

In one embodiment, salicylic acid and pyridine are present in the solution at a final concentration of between 1M and 3M, acid chloride is present in the solution at a final concentration of between 0.5M and 2.0 M prior to precipitation.

In one embodiment, salicylic acid and pyridine are present in the solution at a final concentration of between 1.5M and 2.0M, and acid chloride is present in the solution at a final concentration of between 0.7M and 1.2M prior to precipitation.

EXAMPLES

1. The compound of Formula (I) wherein Y represents —C(=O)—X and X represents —CH$_2$CH$_2$— substituted with the following structure by attachment through the carbon of the —C(O)O group of the structure

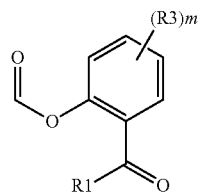

and R and R1 represent —OH,[bis(2-carboxyphenyl) succinate] or BCS, example compound no. 508 in table 1, was synthesised by the following method:

Salicylic acid (27.6 g; 0.2 mol) was added to a 2 neck 250 cm³ Quick-fit round bottom flask. Dry THF (75 cm³; dried over anhydrous magnesium sulphate for 24 h) was then added followed by pyridine (16.1 ml; 0.2 mol). The flask was then fitted with a dropping funnel, condenser and silica-gel guard tubes. The solution was stirred until the salicylic acid had completely dissolved. A solution of succinyl chloride (11.0 cm³; 0.1 mol) in dry THF (20 cm³) was prepared and added slowly (over 20-30 min) with vigorous stirring. Heat was evolved and typically a purple colour developed along with a copious precipitate. Stirring was continued for a further minimum of 1 h, although stirring up to 18 h modestly increases the yield further. The resulting mixture was then poured slowly into ice cold water (300-400 cm³) which was rapidly stirred in a 1l beaker. Stirring was continued (up to 1 h) until the precipitated product was sufficiently crystalline to be filtered with a Buchner apparatus. The crude yield was typically 29.5 g (82%). The product was re-crystallised from ethanol to give a white solid with a melting point of 152-155° C.; the literature value is 155-160° C. (Aldrich catalogue).

The reaction was stirred throughout and the stirring was mechanical stirring.

2. A compound of Formula (I) wherein Y represents H and R represents —NHC(=O)—CH₃, example compound no. 521 in table 1, was synthesised by the following method (after Gordon A. J., *Tetrahedron*, Vol 23, pp 863-870, 1967, Pergamon Press):

Step a)

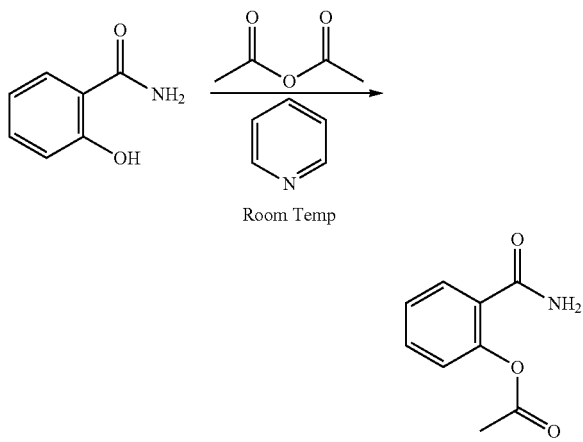

Salicylamide (8.0 g; 0.0584 mol) was mixed with acetic anhydride (20.0 cm³; 0.212 mol) in a conical flask at room temperature. To this solution of pyridine (5.0 cm³; 0.0621 mol) was added and immediately a pale pink solution formed. Within 30 seconds a large amount of white solid was seen. This was filtered under vacuum and washed with toluene, then again with ethyl acetate.

The crude O-acetylsalicylamide was recrystallised from boiling ethyl acetate (solution cooled and stored at −15° C. for 24 h). Yield 8.79 g (84%), mpts 138-144° C. (lit Value 145° C.)

Step b)

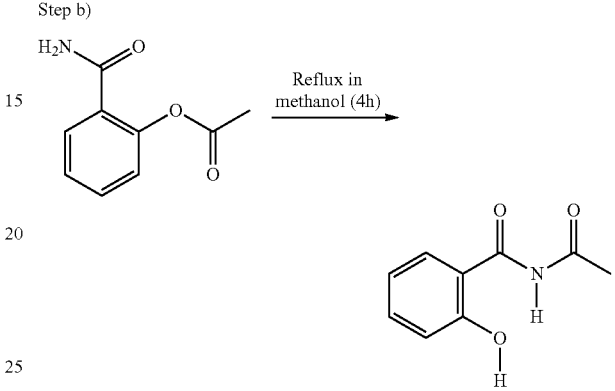

5 g of O-acetylsalicylamide (product of step a)) was refluxed in 25 mls methanol for 4 hours. The methanol was removed by rotary evaporation. The crude product was recrystallised from boiling ethyl acetate (solution cooled to −15° C. for 24 h). Yield 3.4 g (68%), mpt 144-146° C.

These methods are generally applicable to the synthesis of compounds of Formula (I) where the appropriate starting materials are used.

The potential efficacy of compounds of Formula (I) in the treatment of colorectal cancer is illustrated by way of example only, in the following figures. These are merely illustrative and are not intended to limit the scope of the invention in any way.

In general it is envisiaged that for two headed molecules the method of example 1 above would be used with salicylic acid or salicylamide as appropriate and for ingle headed molecules it is envisaged that the method of example 2 would be used.

Figure 2:
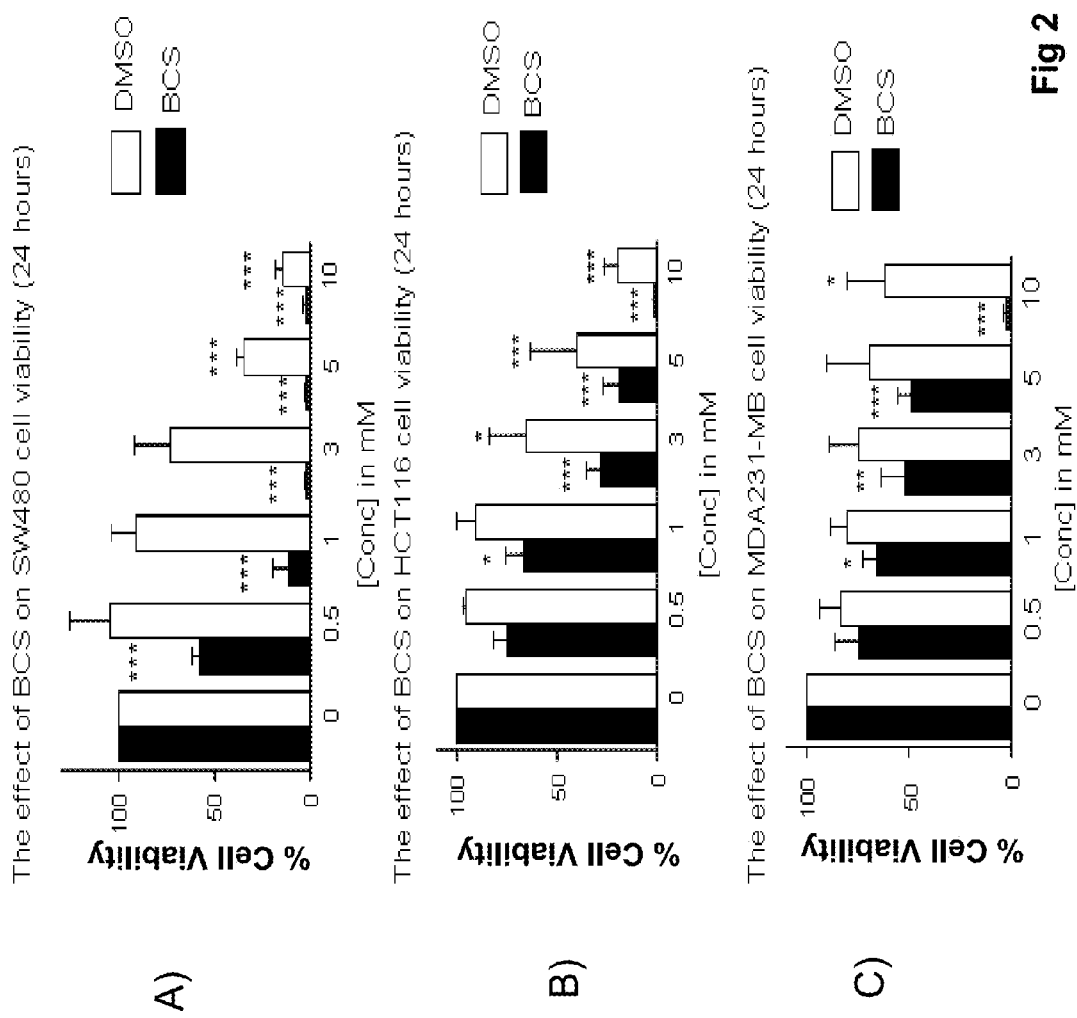
FIG. 2 shows a titration assay illustrating the concentration-effect relationship of a compound of Formula (I) with
A) showing the effect of BCS on SW480 cell viability (24 hours),
B) showing the effect of BCS on HCT116 cell viability (24 hours), and
C) showing the effect of BCS on MDA-231-MB cell viability (24 hours)
Figure 3:
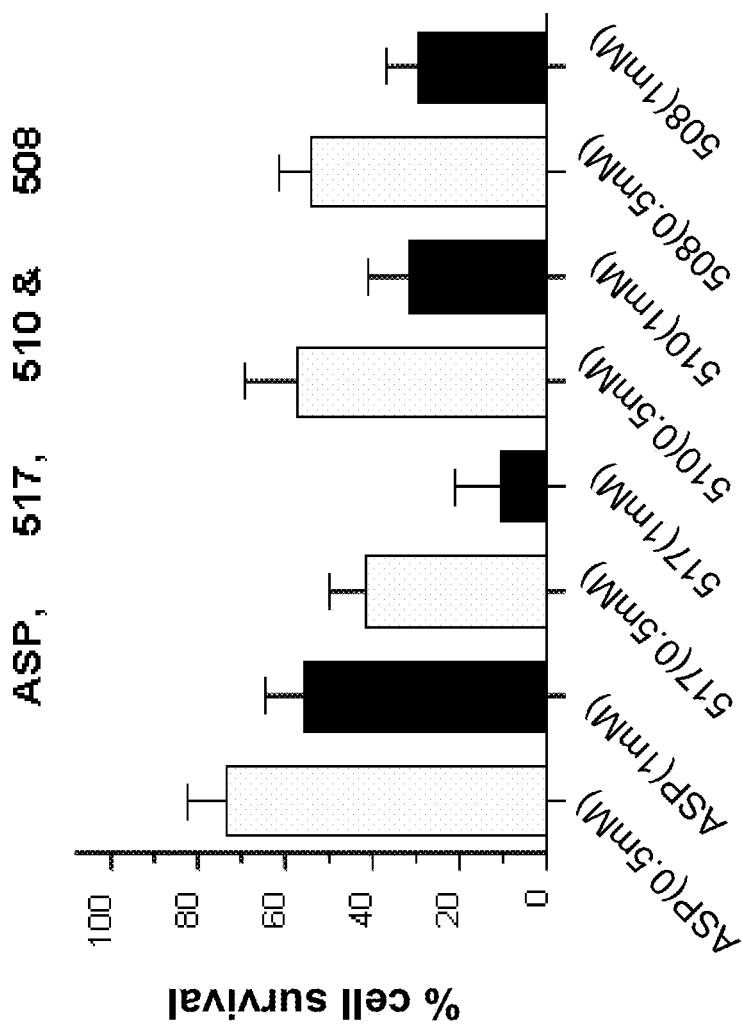
FIG. 3 shows the cytotoxic effect of further compounds of Formula (I)
Figure 4:
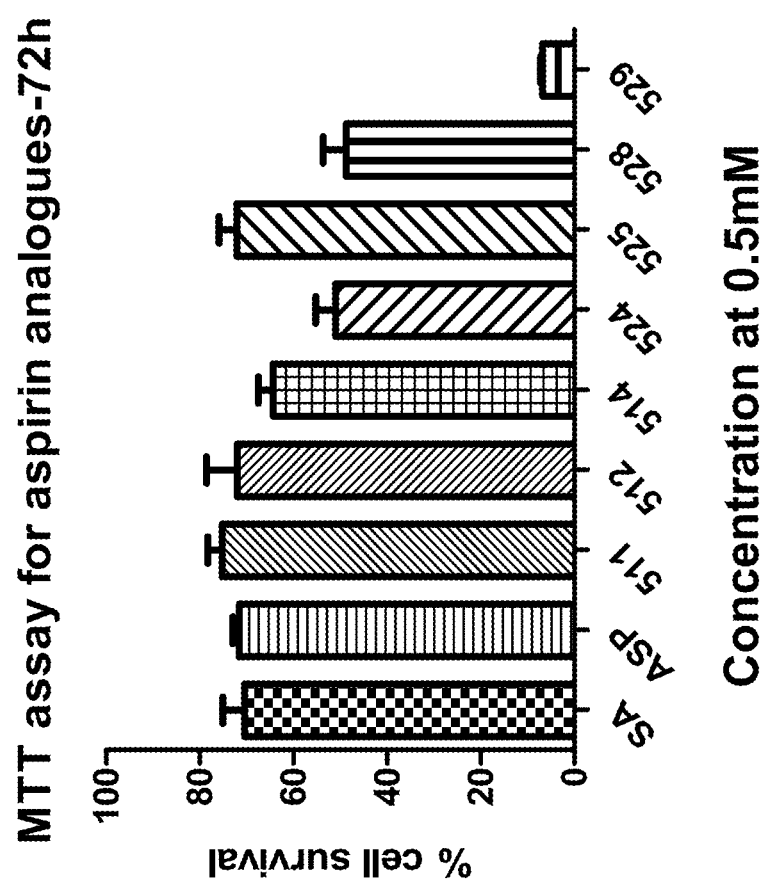
FIG. 4 compares the cytotoxicity of further compounds of Formula (I) all at 0.5 mM and is an MTT assay—72 hours.
Figure 5:
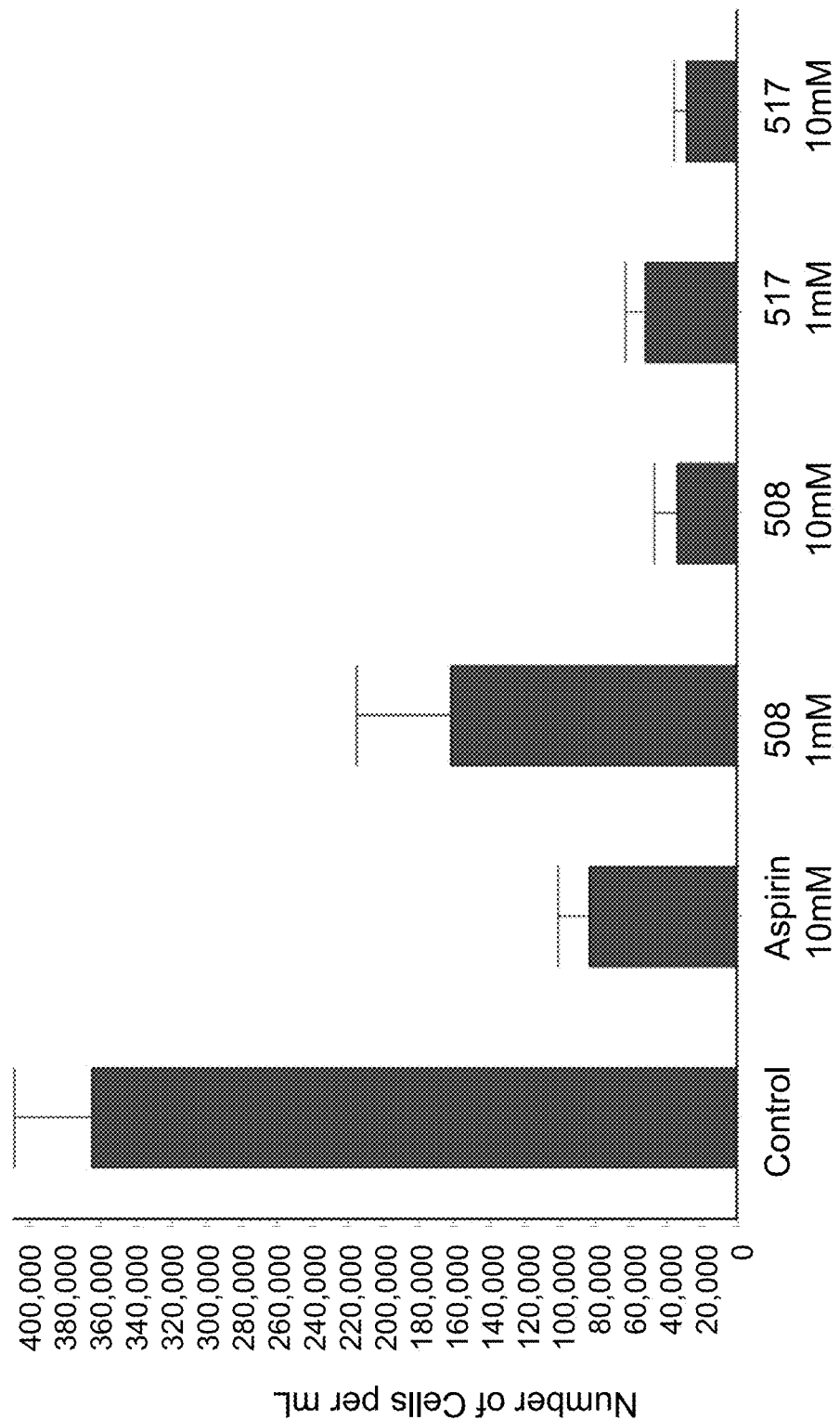
FIG. 5 shows the mean and standard error of the number of MAC 13 cells per ml 48 hours after dosing with various compounds in accordance with the invention.
Figure 6:
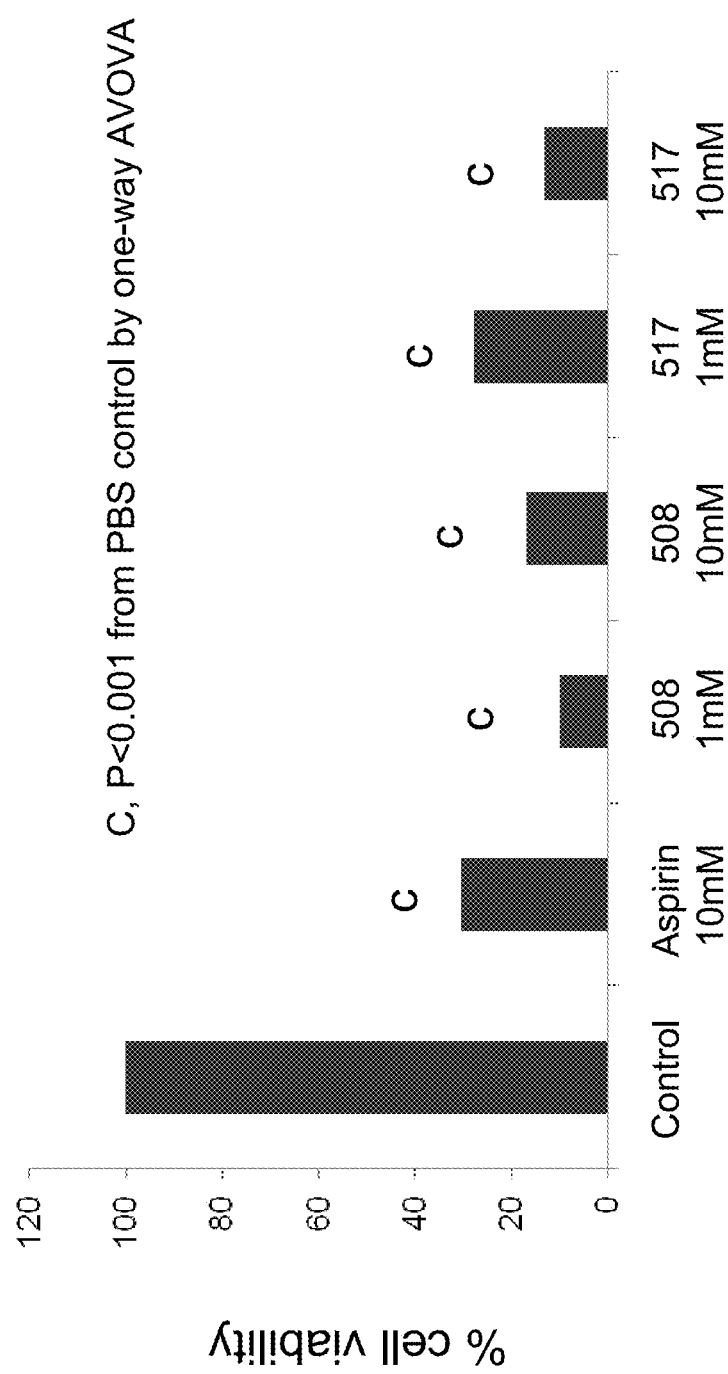
FIG. 6 shows cell viability of MAC 13 tumour cells treated with compounds in accordance with the invention.
Figure 7:
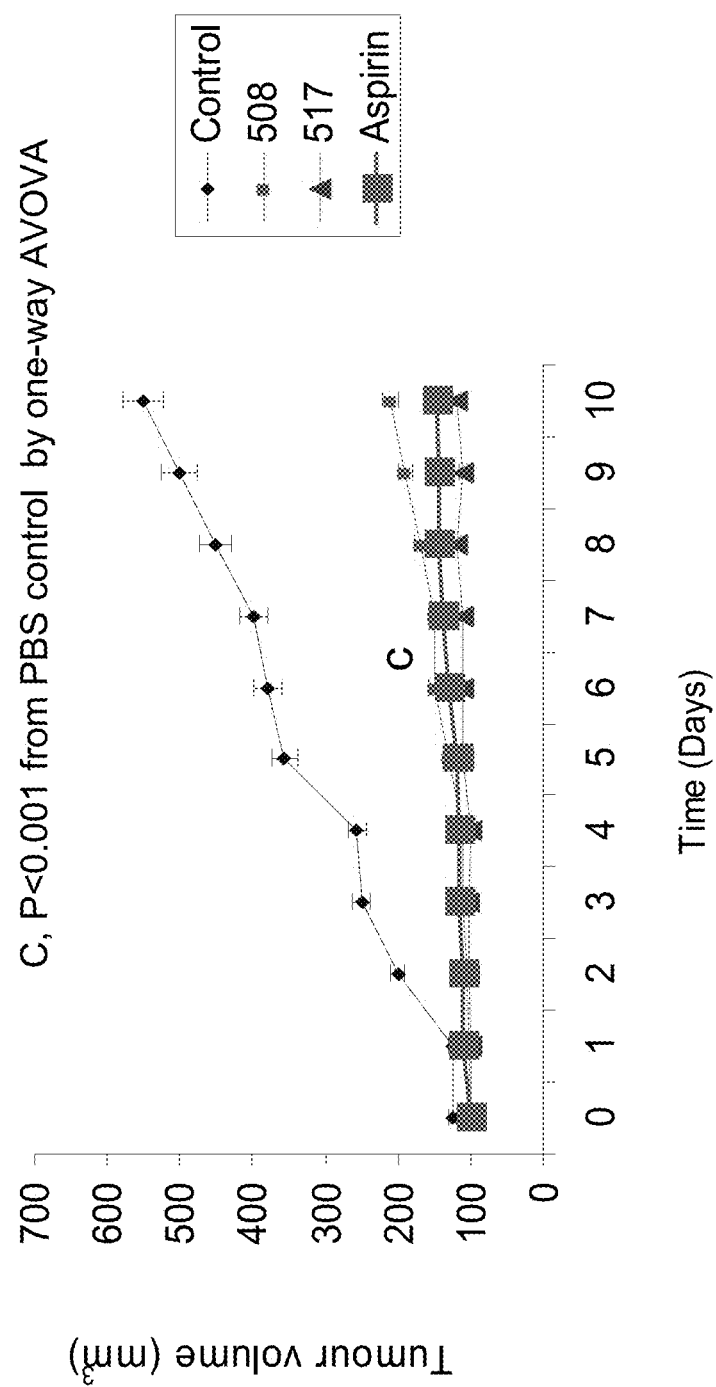
FIG. 7 shows tumour volume in MAC 13 tumour bearing mice treated with and without compounds in accordance with the invention or Aspirin or both.

FIG. 1 shows an in vitro toxicity assay of a compound of Formula (I);

FIG. 2 shows a titration assay illustrating the concentration-effect relationship of a compound of Formula (I) with A) showing the effect of BCS on SW480 cell viability (24 hours), B) showing the effect of BCS on HCT116 cell viability (24 hours), and C) showing the effect of BCS on MDA-231-MB cell viability (24 hours);

FIG. 3 shows the cytotoxic effect of further compounds of Formula (I);

FIG. 4 compares the cytotoxicity of further compounds of Formula (I) all at 0.5 mM and is an MTT assay—72 hours;

FIG. 5 shows the mean and standard error of the number of MAC 13 cells per ml 48 hours after dosing with various compounds in accordance with the invention;

FIG. 6 shows cell viability of MAC 13 tumour cells treated with compounds in accordance with the invention; and FIG. 7 shows tumour volume in MAC 13 tumour bearing mice treated with and without compounds in accordance with the invention or Aspirin or both.

In the examples, assays mentioned are standard cytotoxicity assays and cell cultures used are prepared under standard conditions. The MTT assay referred to is MTT [3-(4,5-Dimethylthiazol-2-yl)-2,5-diphenyltetrazolium-bromide] assay (Mosmann T; J Immunol Methods 65: 55-63, 1983).

Assay Example 1

The cytotoxicity of the BCS, compound 508 of table 1, was tested using an in vitro toxicity assay as shown in FIG. 1. The MTT assay was utilised with a 24 hour incubation period of cell exposure to the compound. Salicylate levels of >1 mM are reported to be achievable in serum in human subjects given analgesic doses of aspirin. Experiments were carried out in triplicate; error bars indicate standard deviation. The SW480 cell line is recognised as a colon carcinoma-derived cell line, MCF-7 cells as a breast cancer-derived cell line and U373MG cells as a cell line derived from a glioma.

Assay Example 2

In FIG. 2, the in vitro toxicity of BCS, compound 508 of table 1, was investigated in further detail by titration against the SW480 colon carcinoma cell line and the DNA mismatch repair deficient HCT-116 colon cancer cell line and the MDA-231MB breast cancer cell line again utilising the MTT assay as described previously. The concentration-effect relationship for the three different cells lines is given in FIG. 2 (error bars indicate mean+/−S.D.). All experiments were performed in triplicate. For clarity, carrier molecule (DMSO) toxicity of the equivalent concentration utilised is also shown. These data indicate that BCS is specifically toxic to colorectal cancer cells.

Assay Example 3

FIG. 3 compares the cytotoxicity of two further compounds of Formula (I) with that of BCS. The first is the adipate ester of a compound of Formula (I) where Y represents —C(=O)—X and X represents —CH$_2$(CH$_2$)$_2$CH$_2$— substituted with the following structure by attachment through the carbon of the —C(O)O group of the structure

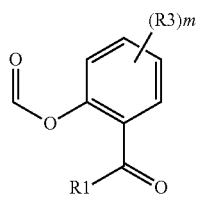

and R and R1 represent —OH (adipoyldiaspirin), example compound no. 510 of table 1, and the second is the fumarate ester of a compound of Formula (I) where Y represents —C(=O)—X and X represents —CH=CH— (trans) substituted with the following structure by attachment through the carbon of the —C(O)O group of the structure

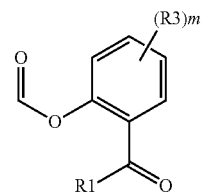

and R and R1 represent —OH (fumaroyldiaspirin), example compound no. 517 of table 1, are shown in FIG. 3 (error bars indicate mean+/−S.D.) and are shown alongside the equivalent concentration of aspirin (as tested using the MTT assay with a 48 hour incubation of cells with compound) and BCS (here termed example compound 508) for comparison. The carrier molecule utilised (DMSO) in these experiments to prepare stock solutions was buffered with Tris-HCl buffer pH8.0 (0.5M) to mitigate against any pH changes caused by the addition of compounds to cell culture medium. All data shown were normalised to cells exposed only to buffered carrier molecule.

BCS is more toxic in comparison to aspirin, yet retains a degree of specificity against the cell line derived from a colon cancer. Aspirin has previously been reported to exhibit toxicity to colorectal cells in vitro. Increased potency in aspirin derivative compounds, the compounds of the invention, is a highly desirable property as the relatively high doses of aspirin needed for colorectal protection are responsible for a number of side effects that are currently a cause for concern when aspirin is administered for a range of therapeutic purposes. These results suggest that aspirin derivatives may represent a possible colorectal therapy combining better efficacy than aspirin with a more favourable side-effect profile.

Assay Example 4

FIG. 4 compares the cytotoxicity of further compounds of Formula (I) all at 0.5 mM. In the following example compounds unless specified otherwise R and R1 are —OH and the compounds can be seen in table 1. For comparison the response to Aspirin and salicylic acid are also shown.

Compound no. 511 is the sebacoyl ester of a compound of Formula (I) where Y represents —C(=O)—X and X represents —CH$_2$(CH$_2$)$_2$CH$_2$— (sebacoyldiaspirin).

Compound no. 512 is the terephthaloyl ester of a compound of Formula (I) where Y represents —C(=O)—X and X represents —(C$_6$H$_4$)— (para) (terephthaloyldiaspirin).

Compound no. 514 is the benzoyl ester of a compound of Formula (I) where Y represents —C(=O)—C$_6$H$_5$ (benzoylaspirin).

Compound no. 524 is the 3-bromobenzoyl ester of a compound of Formula (I) where Y represents —C(=O)—C$_6$H$_4$Br (meta) (m-bromobenzoylaspirin) and compound no. 525 is the 4-methylbenzoyl ester of a compound of Formula (I) where Y represents —C(=O)—C$_6$H$_4$CH$_3$ (para) (p-methylbenzoylaspirin).

Compound no. 528 is the benzoyl ester of a compound of Formula (I) where Y represents —C(=O)—C$_6$H$_5$ and R=—CH$_3$ (methyl ester of benzoylaspirin)

Compound no. 529 is the 3-bromobenzoyl ester of a compound of Formula (I) where Y represents —C(=O)-C$_6$H$_4$Br (meta) and R=—CH(CH$_3$)$_2$ (isopropyl ester of m-bromobenzoylaspirin).

The result shown is the average of three independent experiments (error bars indicate mean+/−SEM). For comparative purposes, compound toxicity is shown alongside the equivalent concentration of salicylic acid (SA) and aspirin (as tested using the MTT assay with a 72 hour incubation of SW480 cells with compound). The carrier molecule utilised in these experiments was DMSO (dimethyl sulphoxide); all data shown were normalised to cells exposed only to carrier molecule.

It can be clearly seen that the compounds of the invention are at least comparable in toxicity with Asprin and some provide much higher toxicity.

Example 5

The results of this example are shown in FIGS. 5 and 6

The murine colon adenocarcinoma cell line (MAC 13) (supplied by John Double at Bradford University) were plated out in equal concentrations in 12-well multi-well plates. 1 ml of Media was used which consisted of RMPI 1640 10% FCS 1% pen/strep and 1% glutamine.

Once the cells reached 90% confluence they were treated with various concentrations of either PBS (phosphate buffered saline), Aspirin, example compound nos. 508 or 517 from table 1 dissolved in PBS.

After 48 h at 5% $CO_2$ and 37° C. the cells were washed in PBS twice before 0.5 ml Typsin-EDTA (10%) was added. Cells were counted using a Coulter Counter. FIG. 6 shows as control.

MTT assays were carried out with MAC 13 cells. Trypan blue was also used as an indicator of viability.

Example 6

The results of this example are shown in FIG. 7.

NMRI mice were treated with MAC13 cells ($5 \times 10^6$) sub cut in their flanks (Hussey H J, Bibby M C, Tisdale M J; British J. of Cancer, 73, 1187-1192, 1996), were treated with example compounds.

Once the tumour was established the tumour was dissected and small fragments re-transplanted into more mice.

The experimental mice were selected at random and given either PBS iv, Aspirin or example compounds nos. 508 or 517 from table 1 dissolved in PBS at (1 mg/kg) the mice weighed approx 20 g.

The mice were monitored daily—weight, food and water consumption and tumour size was recorded using calipers. The experiment ended when the control mouse tumours started to ulcerate.

Prior to the experiment as much as 5 mg/kg was given to several control mice and no toxicity was observed.

In examples 5 and 6 there was obvious cell death and it is postulated by the applicant that this maybe via caspases −3 and −8.

Initial testing as indicated at up to 5 mg/kg in a volume of 100 ul iv in non-tumour bearing NMRI mice caused no side effects. There was no indication of stress, food and water consumption was normal and there was no piloerection.

MAC13 tumour bearing mice were treated with example compounds 508 or 517 from table 1 and there would appear to be a decrease in tumour growth for both 508 and 517 (as seen from FIG. 7).

Example Structures

A selection of example structures according to embodiments of the present invention are set out below:

TABLE 1

| ID No | Structure |
|---|---|
| 503 | (2-(propanoyloxy)benzoic acid structure) |
| 504 | (2-(butanoyloxy)benzoic acid structure) |
| 505 | (2-(pentanoyloxy)benzoic acid structure) |
| 506 | (2-(hexanoyloxy)benzoic acid structure) |
| 507 | (2-(heptanoyloxy)benzoic acid structure) |
| 508 | (bis-salicylate with linker Z; $Z = -CH_2CH_2-$) |
| 509 | (2-((4-hydroxy-4-oxobutanoyl)oxy)benzoic acid structure) |
| 510 | (bis-salicylate with linker Z; $Z = -CH_2(CH_2)_2CH_2-$) |

TABLE 1-continued
| ID No | Structure |
|---|---|
| 511 | 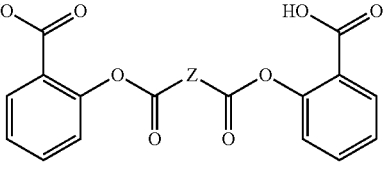 Z = —CH₂(CH₂)₆CH₂— |
| 512 | 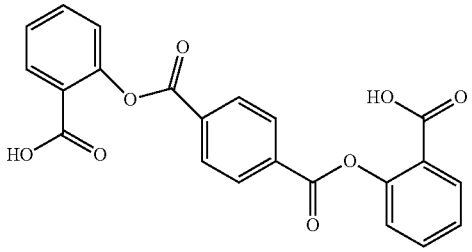 [SMILES: O=C(Oc1ccccc1C(=O)O)c1ccc(C(=O)Oc2ccccc2C(=O)O)cc1] |
| 513 | 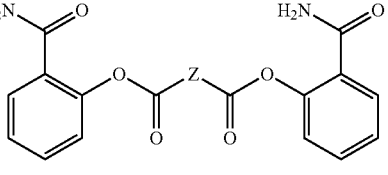 Z = —CH=CH— (trans) |
| 514 | 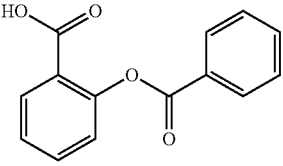 [SMILES: O=C(Oc1ccccc1C(=O)O)c1ccccc1] |
| 515 | 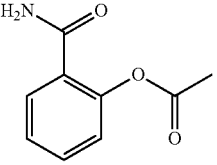 |
| 516 | 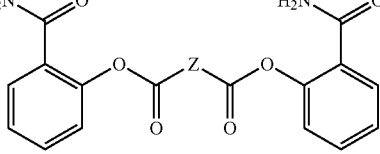 Z = —CH₂CH₂— |
| 517 | 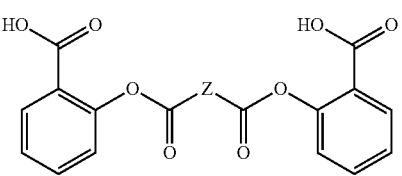 Z = —CH=CH— (trans) |
| 518 | 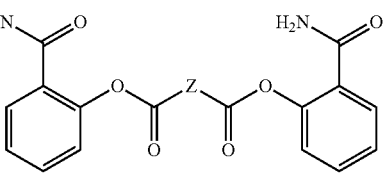 Z = —CH₂(CH₂)₂CH₂— |
| 519 | 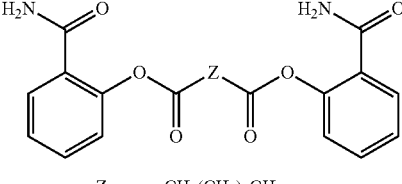 Z = —CH₂(CH₂)₆CH₂— |
| 520 | 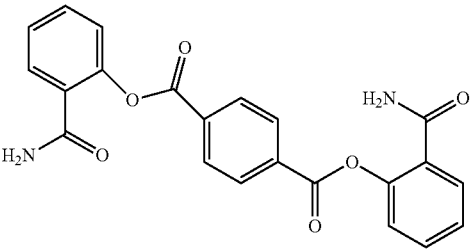 [SMILES: NC(=O)c1ccccc1OC(=O)c1ccc(C(=O)Oc2ccccc2C(N)=O)cc1] |
| 521 | 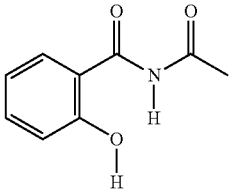 |
| 522 | 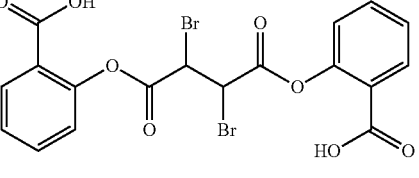 |
| 523 | 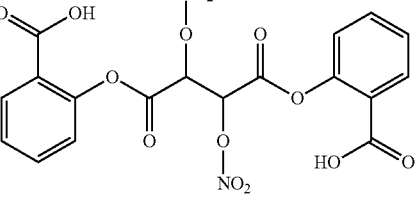 |
| 524 | 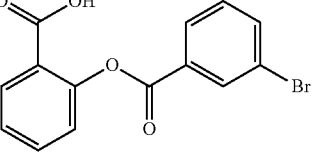 |

TABLE 1-continued

| ID No | Structure |
|---|---|
| 525 | 2-(4-methylbenzoyloxy)benzoic acid |
| 526 | 2-((methoxycarbonyl)oxy)benzoic acid |
| 527 | 2-((ethoxycarbonyl)oxy)benzoic acid |
| 528 | methyl 2-(benzoyloxy)benzoate |
| 529 | isopropyl 2-((3-bromobenzoyl)oxy)benzoate |
| 530 | 2-((phenoxycarbonyl)oxy)benzoic acid |
| 531 | 2-(((4-nitrophenoxy)carbonyl)oxy)benzoic acid |
| 532 | 2-((butoxycarbonyl)oxy)benzoic acid |
| 533 | 2-(((4-chlorobutoxy)carbonyl)oxy)benzoic acid |

The invention claimed is:

1. A method of treating colorectal cancer, comprising administering an effective amount of a compound of Formula (III) or a pharmaceutically acceptable salt, solvate or hydrate thereof, to a patient in need thereof:

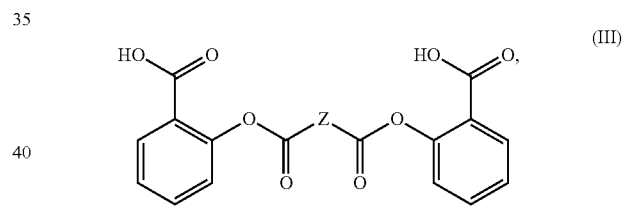

(III)

wherein Z is selected from trans —CH=CH— or —CH$_2$CH$_2$—.

2. The method of claim 1, wherein Z is trans —CH=CH—.

* * * * *